United States Patent
Ward et al.

(10) Patent No.: US 10,513,476 B2
(45) Date of Patent: *Dec. 24, 2019

(54) PROCESS AND INSTALLATION FOR THE CONVERSION OF CRUDE OIL TO PETROCHEMICALS HAVING AN IMPROVED PROPYLENE YIELD

(71) Applicants: SAUDI BASIC INDUSTRIES CORPORATION, Riyadh (SA); SABIC GLOBAL TECHNOLOGIES B.V., Bergen op Zoom (NL)

(72) Inventors: Andrew Mark Ward, Wilton Centre (GB); Ravichander Narayanaswamy, Bangalore (IN); Vijayanand Rajagopalan, Bangalore (IN); Arno Johannes Maria Oprins, Geleen (NL); Egidius Jacoba Maria Schaerlaeckens, Geleen (NL); Raul Velasco Pelaez, Geleen (NL)

(73) Assignees: SAUDI BASIC INDUSTRIES CORPORATION, Riyadh (SA); SABIC GLOBAL TECHNOLOGIES B.V., Bergen op Zoom (NL)

( * ) Notice: Subject to any disclaimer, the term of this patent is extended or adjusted under 35 U.S.C. 154(b) by 0 days.

This patent is subject to a terminal disclaimer.

(21) Appl. No.: 16/153,125

(22) Filed: Oct. 5, 2018

(65) Prior Publication Data
US 2019/0039969 A1 Feb. 7, 2019

Related U.S. Application Data

(63) Continuation of application No. 14/901,852, filed as application No. PCT/EP2014/063855 on Jun. 30, 2014, now Pat. No. 10,138,177.

(30) Foreign Application Priority Data

Jul. 2, 2013 (EP) .................................... 13174751

(51) Int. Cl.
*C07C 2/76* (2006.01)
*C07C 5/02* (2006.01)
(Continued)

(52) U.S. Cl.
CPC .................. *C07C 4/04* (2013.01); *C10G 7/00* (2013.01); *C10G 9/00* (2013.01); *C10G 9/36* (2013.01);
(Continued)

(58) Field of Classification Search
CPC .... C07C 2/76; C07C 5/02; C07C 4/04; C10G 63/00; C10G 63/04; C10G 63/06; C10G 63/08
(Continued)

(56) References Cited

U.S. PATENT DOCUMENTS 2,761,825 A 9/1956 Schultz
3,256,176 A 6/1966 Mills et al.
(Continued)

FOREIGN PATENT DOCUMENTS

EP 0192059 8/1986
EP 0909804 4/1999
(Continued)

OTHER PUBLICATIONS

Alfke et al. (2007) Oil Refining, Ullmann's Encyclopedia of Industrial Chemistry.
(Continued)

*Primary Examiner* — Thuan D Dang
(74) *Attorney, Agent, or Firm* — Norton Rose Fulbright US LLP (57) ABSTRACT

The present invention relates to an integrated process to convert crude oil into petrochemical products comprising crude oil distillation, aromatic ring opening, and olefins synthesis, which process comprises subjecting a hydrocarbon feed to aromatic ring opening to produce LPG and subjecting the LPG produced in the integrated process to olefins synthesis. Furthermore, the present invention relates to a process installation to convert crude oil into petrochemical products comprising a crude distillation unit comprising an inlet for crude oil and at least one outlet for kerosene and/or gasoil; an aromatic ring opening unit comprising an inlet for a hydrocarbon feed to aromatic ring opening and an outlet for LPG; and a unit for the olefins synthesis comprising an inlet for LPG produced by the integrated petrochemical process installation and an outlet for olefins. The hydrocarbon feed subjected to aromatic ring opening comprises kerosene and/or gasoil produced by crude oil distillation in the process; and refinery unit-derived middle-distillate produced in the process. The process and the process installation of the present invention have an increased production of petrochemicals at the expense of the production of fuels and an improved propylene yield.

17 Claims, 2 Drawing Sheets

(51) Int. Cl.

| | | |
|---|---|---|
| C07C 4/04 | (2006.01) | |
| C10G 45/58 | (2006.01) | |
| C10G 69/00 | (2006.01) | |
| C10G 69/04 | (2006.01) | |
| C10G 69/06 | (2006.01) | |
| C10G 9/00 | (2006.01) | |
| C10G 7/00 | (2006.01) | |
| C10G 55/02 | (2006.01) | |
| C10G 9/36 | (2006.01) | |

(52) U.S. Cl.
CPC .............. *C10G 45/58* (2013.01); *C10G 55/02* (2013.01); *C10G 69/00* (2013.01); *C10G 69/04* (2013.01); *C10G 69/06* (2013.01); *C10G 2400/20* (2013.01); *Y02P 20/125* (2015.11)

(58) Field of Classification Search
USPC ...... 585/324, 648, 652, 752; 208/49, 59, 58, 208/78, 80
See application file for complete search history.

(56) References Cited

U.S. PATENT DOCUMENTS

| 3,702,292 A | 11/1972 | Burich |
|---|---|---|
| 3,839,484 A | 10/1974 | Zimmerman et al. |
| 3,944,481 A | 3/1976 | Wing et al. |
| 4,150,061 A | 4/1979 | Feinstein et al. |
| 4,181,601 A | 1/1980 | Sze |
| 4,341,622 A | 7/1982 | Tabak et al. |
| 4,575,575 A | 3/1986 | Drake et al. |
| 4,789,457 A | 12/1988 | Ficher et al. |
| 5,846,402 A | 12/1998 | Mandal et al. |
| 6,067,910 A | 5/2000 | Theurer et al. |
| 6,153,087 A | 11/2000 | Bigeard et al. |
| 6,270,654 B1 | 8/2001 | Colyar et al. |
| 7,067,448 B1 | 6/2006 | Weitkamp et al. |
| 7,214,308 B2 | 5/2007 | Colyar |
| 7,622,623 B2 | 11/2009 | Fridman et al. |
| 7,704,377 B2 | 4/2010 | Duddy et al. |
| 7,813,988 B2 | 10/2010 | Levin et al. |
| 7,938,952 B2 | 5/2011 | Colyar et al. |
| 8,926,824 B2 | 1/2015 | Morel |
| 9,005,430 B2 | 4/2015 | Fournier et al. |
| 9,840,674 B2 | 12/2017 | Weiss et al. |
| 2004/0199039 A1 | 10/2004 | Brophy et al. |
| 2005/0101814 A1 | 5/2005 | Foley et al. |
| 2007/0062848 A1 | 3/2007 | Oballa et al. |
| 2008/0093262 A1 | 4/2008 | Gragnani et al. |
| 2010/0300932 A1 | 12/2010 | Debuisschert et al. |
| 2012/0000819 A1 | 1/2012 | Matsushita |
| 2012/0241358 A1 | 9/2012 | Al-Thubaiti et al. |
| 2014/0299515 A1 | 10/2014 | Weiss et al. |
| 2016/0122666 A1 | 5/2016 | Weiss et al. |

FOREIGN PATENT DOCUMENTS

| GB | 1248814 | 5/1969 |
|---|---|---|
| GB | 2162082 | 1/1986 |
| JP | S52-095601 | 8/1977 |
| JP | S60-004136 | 1/1985 |
| JP | 2005-325263 | 11/2005 |
| JP | 2009-508881 | 3/2009 |
| WO | WO 2016/146326 | 9/2016 |

OTHER PUBLICATIONS

Haizmann, Robert "Maximize Conversion and Flexibility, The UOP Uniflex Process" 6th Russia & CIS BBTC Conference, Apr. 13-14, 2011.
International Search Report for International Application No. PCT/EP2014/063855; International Filing Date: Jun. 30, 2014; dated Oct. 13, 2014; 5 pages.
Office Action issued in Japanese Patent Application No. 2016-522565, dated Jul. 3, 2018.
Speight (2005) Petroleum Refinery Process, Kirk-Othmer Encyclopedia of Chemcial Technology.
WayBack "Bitesize"; Jul. 2012; 2 pages.
WayBack Wikipedia "Fuel Oil" 2017, 10 pages.
WayBack Wikipedia "Kerosene" 2017, 11 pages.
Written Opinion of the International Search Authority for International Application No. PCT/EP2014/063855; International Filing Date: Jun. 30, 2014; dated Oct. 13, 2014; 6 Pages.

PROCESS AND INSTALLATION FOR THE CONVERSION OF CRUDE OIL TO PETROCHEMICALS HAVING AN IMPROVED PROPYLENE YIELD

CROSS-REFERENCE TO RELATED APPLICATIONS

This application is a continuation of U.S. application Ser. No. 14/901,852 which is a national phase under 35 U.S.C. § 371 of International Application No. PCT/EP2014/063855, filed Jun. 30, 2014, which claims the benefit of priority to European Application Serial No. 13174751.1, filed Jul. 2, 2013, the entire contents of each of which are hereby incorporated by reference in their entirety.

FIELD OF THE INVENTION

The present invention relates to an integrated process to convert crude oil into petrochemical products comprising crude oil distillation, aromatic ring opening, and olefins synthesis. Furthermore, the present invention relates to a process installation to convert crude oil into petrochemical products comprising a crude distillation unit, a aromatic ring opening unit and a unit for olefins synthesis.

BACKGROUND OF THE INVENTION

It has been previously described that a crude oil refinery can be integrated with downstream chemical plants such as a pyrolysis steam cracking unit in order to increase the production of high-value chemicals at the expense of the production of fuels.

U.S. Pat. No. 3,702,292 describes an integrated crude oil refinery arrangement for producing fuel and chemical products, involving crude oil distillation means, hydrocracking means, delayed coking means, reforming means, ethylene and propylene producing means comprising a pyrolysis steam cracking unit and a pyrolysis products separation unit, catalytic cracking means, aromatic product recovery means, butadiene recovery means and alkylation means in an interrelated system to produce a conversion of crude oil to petrochemicals of about 50% and a conversion of crude oil to fuels of about 50%.

A major drawback of conventional means and methods to integrate oil refinery operations with downstream chemical plants to produce petrochemicals is that such integrated processes still produce significant amounts of fuel. Furthermore, conventional means and methods to integrate oil refinery operations with downstream chemical plants have a relatively low propylene yield in terms of wt-% of crude.

OBJECTS OF THE INVENTION

It was an object of the present invention to provide a means and methods to integrate oil refinery operations with downstream chemical plants which has an increased production of petrochemicals at the expense of the production of fuels. It was furthermore an object of the present invention to provide a means and methods to integrate oil refinery operations with downstream chemical plants which has an improved propylene yield.

SUMMARY OF THE INVENTION

The solution to the above problem is achieved by providing the embodiments as described herein below and as characterized in the claims.

In one aspect, the present invention relates to an integrated process to convert crude oil into petrochemical products. This process is also presented in FIGS. 1-3 which are further described herein below.

DETAILED DESCRIPTION

Accordingly, the present invention provides an integrated process to convert crude oil into petrochemical products comprising crude oil distillation, aromatic ring opening and olefins synthesis, which process comprises subjecting a hydrocarbon feed to aromatic ring opening to produce LPG and subjecting the LPG produced in the integrated process to olefins synthesis, wherein said hydrocarbon feed comprises:

kerosene and/or gasoil produced by crude oil distillation in the process; and refinery unit-derived middle-distillate produced in the process.

Conventionally, petrochemical products, such as propylene, are produced by subjecting crude oil to crude oil distillation and to subject specific crude oil fractions thus obtained to a refinery process. In the context of the present invention, it was found that the propylene yield of a process to convert crude oil into petrochemical products can be improved by subjecting one or more of naphtha, kerosene and gasoil to aromatic ring opening and subsequently converting the LPG produced by aromatic ring opening into olefins, when compared to subjecting the same crude oil fractions directly to steam cracking. As used herein, the term "propylene yield" relates to the wt-% of propylene produced of the total mass of the crude. Furthermore, by first converting the hydrocarbon feedstock to LPG before subjecting to olefin synthesis, the fractionation section downstream of the olefin synthesis unit can be much less complex since much less by-products, such as carbon black oil or cracked distillate, are produced which leads to greatly reduced capital expenditures.

Accordingly, the term "kerosene and/or gasoil produced by crude oil distillation in the process" means that said one or more of kerosene and gasoil are produced by the crude distillation process step comprised in the integrated process of the present invention. Moreover, the term "refinery unit-derived middle-distillate produced in the process" means that said refinery unit-derived middle-distillate are produced by a refinery unit process step comprised in the integrated process of the present invention.

The prior art describes processes for producing petrochemical products from specific hydrocarbon feeds such as specific crude oil fractions and/or refinery unit-derived distillates.

U.S. Pat. No. 3,839,484 describes a process for the preparation of unsaturated hydrocarbons by pyrolysis of naphthas in a pyrolysis furnace comprising hydrocracking said naphthas to form a mixture of paraffins and isoparaffins said mixture consisting essentially of hydrocarbons containing from 1 to about 7 carbon atoms per molecule and pyrolyzing the resulting mixture of paraffins and isoparaffins in said pyrolysis furnace. The process of U.S. Pat. No. 3,839,484 further describes that the diesel fuel and distillate fuels boiling in the range of 400-650° F. (about 204-343° C.) are not further processed.

The term "crude oil" as used herein refers to the petroleum extracted from geologic formations in its unrefined form. The term crude oil will also be understood to include that which has been subjected to water-oil separations and/or gas-oil separation and/or desalting and/or stabilization. Any crude oil is suitable as the source material for the process of this invention, including Arabian Heavy, Arabian Light, other Gulf crudes, Brent, North Sea crudes, North and West African crudes, Indonesian, Chinese crudes and mixtures thereof, but also shale oil, tar sands, gas condensates and bio-based oils. The crude oil used as feed to the process of the present invention preferably is conventional petroleum having an API gravity of more than 20° API as measured by the ASTM D287 standard. More preferably, the crude oil used in the process of the present invention is a light crude oil having an API gravity of more than 30° API. Most preferably, the crude oil used in the process of the present invention comprises Arabian Light Crude Oil. Arabian Light Crude Oil typically has an API gravity of between 32-36° API and a sulfur content of between 1.5-4.5 wt-%.

The term "petrochemicals" or "petrochemical products" as used herein relates to chemical products derived from crude oil that are not used as fuels. Petrochemical products include olefins and aromatics that are used as a basic feedstock for producing chemicals and polymers. High-value petrochemicals include olefins and aromatics. Typical high-value olefins include, but are not limited to, ethylene, propylene, butadiene, butylene-1, isobutylene, isoprene, cyclopentadiene and styrene. Typical high-value aromatics include, but are not limited to, benzene, toluene, xylene and ethyl benzene.

The term "fuels" as used herein relates to crude oil-derived products used as energy carrier. Unlike petrochemicals, which are a collection of well-defined compounds, fuels typically are complex mixtures of different hydrocarbon compounds. Fuels commonly produced by oil refineries include, but are not limited to, gasoline, jet fuel, diesel fuel, heavy fuel oil and petroleum coke.

The term "gases produced by the crude distillation unit" or "gases fraction" as used herein refers to the fraction obtained in a crude oil distillation process that is gaseous at ambient temperatures. Accordingly, the "gases fraction" derived by crude distillation mainly comprises C1-C4 hydrocarbons and may further comprise impurities such as hydrogen sulfide and carbon dioxide. In this specification, other petroleum fractions obtained by crude oil distillation are referred to as "naphtha", "kerosene", "gasoil" and "resid". The terms naphtha, kerosene, gasoil and resid are used herein having their generally accepted meaning in the field of petroleum refinery processes; see Alfke et al. (2007) Oil Refining, Ullmann's Encyclopedia of Industrial Chemistry and Speight (2005) Petroleum Refinery Processes, Kirk-Othmer Encyclopedia of Chemical Technology. In this respect, it is to be noted that there may be overlap between the different crude oil distillation fractions due to the complex mixture of the hydrocarbon compounds comprised in the crude oil and the technical limits to the crude oil distillation process. Preferably, the term "naphtha" as used herein relates to the petroleum fraction obtained by crude oil distillation having a boiling point range of about 20-200° C., more preferably of about 30-190° C. Preferably, light naphtha is the fraction having a boiling point range of about 20-100° C., more preferably of about 30-90° C. Heavy naphtha preferably has a boiling point range of about 80-200° C., more preferably of about 90-190° C. Preferably, the term "kerosene" as used herein relates to the petroleum fraction obtained by crude oil distillation having a boiling point range of about 180-270° C., more preferably of about 190-260° C. Preferably, the term "gasoil" as used herein relates to the petroleum fraction obtained by crude oil distillation having a boiling point range of about 250-360° C., more preferably of about 260-350° C. Preferably, the term "resid" as used herein relates to the petroleum fraction obtained by crude oil distillation having a boiling point of more than about 340° C., more preferably of more than about 350° C.

As used herein, the term "refinery unit" relates to a section of a petrochemical plant complex for the chemical conversion of crude oil to petrochemicals and fuels. In this respect, it is to be noted that a unit for olefins synthesis, such as a steam cracker, is also considered to represent a "refinery unit". In this specification, different hydrocarbons streams produced by refinery units or produced in refinery unit operations are referred to as: refinery unit-derived gases, refinery unit-derived light-distillate, refinery unit-derived middle-distillate and refinery unit-derived heavy-distillate. Accordingly, a refinery unit derived distillate is obtained as the result of a chemical conversion followed by a separation, e.g. by distillation or by extraction, which is in contrast to a crude oil fraction. The term "refinery unit-derived gases" relates to the fraction of the products produced in a refinery unit that is gaseous at ambient temperatures. Accordingly, the refinery unit-derived gas stream may comprise gaseous compounds such as LPG and methane. Other components comprised in the refiner unit-derived gas stream may be hydrogen and hydrogen sulfide. The terms light-distillate, middle-distillate and heavy-distillate are used herein having their generally accepted meaning in the field of petroleum refinery processes; see Speight, J. G. (2005) loc.cit. In this respect, it is to be noted that there may be overlap between different distillation fractions due to the complex mixture of the hydrocarbon compounds comprised in the product stream produced by refinery unit operations and the technical limits to the distillation process used to separate the different fractions. Preferably, the refinery-unit derived light-distillate is the hydrocarbon distillate obtained in a refinery unit process having a boiling point range of about 20-200° C., more preferably of about 30-190° C. The "light-distillate" is often relatively rich in aromatic hydrocarbons having one aromatic ring. Preferably, the refinery-unit derived middle-distillate is the hydrocarbon distillate obtained in a refinery unit process having a boiling point range of about 180-360° C., more preferably of about 190-350° C. The "middle-distillate" is relatively rich in aromatic hydrocarbons having two aromatic rings. Preferably, the refinery-unit derived heavy-distillate is the hydrocarbon distillate obtained in a refinery unit process having a boiling point of more than about 340° C., more preferably of more than about 350° C. The "heavy-distillate" is relatively rich in hydrocarbons having condensed aromatic rings.

The term "aromatic hydrocarbons" or "aromatics" is very well known in the art. Accordingly, the term "aromatic hydrocarbon" relates to cyclically conjugated hydrocarbon with a stability (due to delocalization) that is significantly greater than that of a hypothetical localized structure (e.g. Kekulé structure). The most common method for determining aromaticity of a given hydrocarbon is the observation of diatropicity in the 1H NMR spectrum, for example the presence of chemical shifts in the range of from 7.2 to 7.3 ppm for benzene ring protons.

The terms "naphthenic hydrocarbons" or "naphthenes" or "cycloalkanes" is used herein having its established meaning and accordingly relates to types of alkanes that have one or more rings of carbon atoms in the chemical structure of their molecules.

The term "olefin" is used herein having its well-established meaning. Accordingly, olefin relates to an unsaturated hydrocarbon compound containing at least one carbon-carbon double bond. Preferably, the term "olefins" relates to a mixture comprising two or more of ethylene, propylene, butadiene, butylene-1, isobutylene, isoprene and cyclopentadiene.

One of the petrochemical products produced in the process of the present invention is BTX. The term "LPG" as used herein refers to the well-established acronym for the term "liquefied petroleum gas". LPG generally consists of a blend of C2-C4 hydrocarbons i.e. a mixture of C2, C3, and C4 hydrocarbons. Preferably, the product produced in the process of the present invention comprises further useful aromatic hydrocarbons such as ethylbenzene. Accordingly, the present invention preferably provides a process for producing a mixture of benzene, toluene xylenes and ethylbenzene ("BTXE"). The product as produced may be a physical mixture of the different aromatic hydrocarbons or may be directly subjected to further separation, e.g. by distillation, to provide different purified product streams. Such purified product stream may include a benzene product stream, a toluene product stream, a xylene product stream and/or an ethylbenzene product stream.

The term "BTX" as used herein relates to a mixture of benzene, toluene and xylenes.

As used herein, the term "C# hydrocarbons", wherein "#" is a positive integer, is meant to describe all hydrocarbons having # carbon atoms. Moreover, the term "C#+ hydrocarbons" is meant to describe all hydrocarbon molecules having # or more carbon atoms. Accordingly, the term "C5+ hydrocarbons" is meant to describe a mixture of hydrocarbons having 5 or more carbon atoms. The term "C5+ alkanes" accordingly relates to alkanes having 5 or more carbon atoms.

The process of the present invention involves crude distillation, which comprises separating different crude oil fractions based on a difference in boiling point. As used herein, the term "crude distillation unit" or "crude oil distillation unit" relates to the fractionating column that is used to separate crude oil into fractions by fractional distillation; see Alfke et al. (2007) loc.cit. Preferably, the crude oil is processed in an atmospheric distillation unit to separate gas oil and lighter fractions from higher boiling components (atmospheric residuum or "resid"). In the present invention, it is not required to pass the resid to a vacuum distillation unit for further fractionation of the resid, and it is possible to process the resid as a single fraction. In case of relatively heavy crude oil feeds, however, it may be advantageous to further fractionate the resid using a vacuum distillation unit to further separate the resid into a vacuum gas oil fraction and vacuum residue fraction. In case vacuum distillation is used, the vacuum gas oil fraction and vacuum residue fraction may be processed separately in the subsequent refinery units. For instance, the vacuum residue fraction may be specifically subjected to solvent deasphalting before further processing. Preferably, the term "vacuum gas oil" as used herein relates to the petroleum fraction obtained by crude oil distillation having a having a boiling point range of about 340-560° C., more preferably of about 350-550° C. Preferably, the term "vacuum resid" as used herein relates to the petroleum fraction obtained by crude oil distillation having a boiling point of more than about 540° C., more preferably of more than about 550° C.

The "aromatic ring opening unit" refers to a refinery unit wherein the aromatic ring opening process is performed. Aromatic ring opening is a specific hydrocracking process that is particularly suitable for converting a feed that is relatively rich in aromatic hydrocarbon having a boiling point in the kerosene and gasoil boiling point range, and optionally the vacuum gasoil boiling point range, to produce LPG and, depending on the specific process and/or process conditions, a light-distillate (ARO-derived gasoline). Such an aromatic ring opening process (ARO process) is for instance described in U.S. Pat. Nos. 3,256,176 and 4,789,457. Such processes may comprise of either a single fixed bed catalytic reactor or two such reactors in series together with one or more fractionation units to separate desired products from unconverted material and may also incorporate the ability to recycle unconverted material to one or both of the reactors. Reactors may be operated at a temperature of 200-600° C., preferably 300-400° C., a pressure of 3-35 MPa, preferably 5 to 20 MPa together with 5-20 wt-% of hydrogen (in relation to the hydrocarbon feedstock), wherein said hydrogen may flow co-current with the hydrocarbon feedstock or counter current to the direction of flow of the hydrocarbon feedstock, in the presence of a dual functional catalyst active for both hydrogenation-dehydrogenation and ring cleavage, wherein said aromatic ring saturation and ring cleavage may be performed. Catalysts used in such processes comprise one or more elements selected from the group consisting of Pd, Rh, Ru, Ir, Os, Cu, Co, Ni, Pt, Fe, Zn, Ga, In, Mo, W and V in metallic or metal sulphide form supported on an acidic solid such as alumina, silica, alumina-silica and zeolites. In this respect, it is to be noted that the term "supported on" as used herein includes any conventional way to provide a catalyst which combines one or more elements with a catalytic support. By adapting either single or in combination the catalyst composition, operating temperature, operating space velocity and/or hydrogen partial pressure, the process can be steered towards full saturation and subsequent cleavage of all rings or towards keeping one aromatic ring unsaturated and subsequent cleavage of all but one ring. In the latter case, the ARO process produces a light-distillate ("ARO-gasoline") which is relatively rich in hydrocarbon compounds having one aromatic and or naphthenic ring. In the context of the present invention, it is preferred to use an aromatic ring opening process that is optimized to open all aromatic rings and thus to produce LPG at the expense of a light-distillate which is relatively rich in hydrocarbon compounds having one aromatic ring. Yet, also in a mode wherein all aromatic rings are opened, the ARO process may still produce small amounts of distillates, which are preferably recycled to refinery units capable of processing and upgrading said distillates to petrochemicals or to intermediate products that can be further upgraded to petrochemicals. A further aromatic ring opening process (ARO process) is described in U.S. Pat. No. 7,513,988. Accordingly, the ARO process may comprise aromatic ring saturation at a temperature of 100-500° C., preferably 200-500° C., more preferably 300-500° C., a pressure of 2-10 MPa together with 5-30 wt-%, preferably 10-30 wt-% of hydrogen (in relation to the hydrocarbon feedstock) in the presence of an aromatic hydrogenation catalyst and ring cleavage at a temperature of 200-600° C., preferably 300-400° C., a pressure of 1-12 MPa together with 5-20 wt-% of hydrogen (in relation to the hydrocarbon feedstock) in the presence of a ring cleavage catalyst, wherein said aromatic ring saturation and ring cleavage may be performed in one reactor or in two consecutive reactors. The aromatic hydrogenation catalyst may be a conventional hydrogenation/hydrotreating catalyst such as a catalyst comprising a mixture of Ni, W and Mo on a refractory support, typically alumina. The ring cleavage catalyst comprises a transition metal or metal sulphide component and a support. Preferably the catalyst comprises one or more elements selected from the group consisting of Pd, Rh, Ru, Ir, Os, Cu, Co, Ni, Pt, Fe, Zn, Ga, In, Mo, W and V in metallic or metal sulphide form supported on an acidic solid such as alumina, silica, alumina-silica and zeolites. By adapting either single or in combination the catalyst composition, operating temperature, operating space velocity and/or hydrogen partial pressure, the process can be steered towards full saturation and subsequent cleavage of all rings or towards keeping one aromatic ring unsaturated and subsequent cleavage of all but one ring. In the latter case, the ARO process produces a light-distillate ("ARO-gasoline") which is relatively rich in hydrocarbon compounds having one aromatic ring. In the context of the present invention, it is preferred to use an aromatic ring opening process that is optimized to open all aromatic rings and thus to produce LPG at the expense of a light-distillate which is relatively rich in hydrocarbon compounds having one aromatic ring. Yet, also in a mode wherein all aromatic rings are opened, the ARO process may still produce small amounts of distillates, which are preferably recycled to refinery units capable of processing and upgrading said distillates to petrochemicals or to intermediate products that can be further upgraded to petrochemicals. Other examples of aromatic ring opening processes to produce LPG are described in U.S. Pat. No. 7,067,448 and US 2005/0101814.

By steering the aromatic ring opening process towards full saturation and subsequent cleavage of all rings or towards keeping one aromatic ring unsaturated and subsequent cleavage of all but one ring, the ratio of olefins produced and aromatics produced in the process of the present invention can be steered so that a neutral hydrogen balance can be obtained, depending on hydrogen balance of the feed. With hydrogen-rich feeds, such as shale oil, (almost) no aromatics have to be produced to obtain hydrogen balanced overall process.

The hydrocarbon feed to aromatic ring opening used in the process of the present invention preferably comprises kerosene and gasoil produced by crude oil distillation in the process and refinery unit-derived middle-distillate produced in the process. More preferably, the hydrocarbon feed to aromatic ring opening used in the process of the present invention comprises naphtha, kerosene and gasoil produced by crude oil distillation in the process and refinery unit-derived light-distillate and refinery unit-derived middle-distillate produced in the process.

The LPG produced in the process that is subjected to olefins synthesis preferably comprises LPG comprised in the gases fraction derived by crude oil distillation and LPG comprised in the refinery unit-derived gases.

Preferably, the process of the present invention comprises:
(a) subjecting crude oil to crude oil distillation to produce gases fraction, resid and one or more of kerosene and gasoil;
(b) subjecting resid to resid upgrading to produce LPG and a liquid resid upgrading effluent;
(c) subjecting liquid resid upgrading effluent and one or more selected from the group consisting of kerosene and gasoil to aromatic ring opening to produce LPG; and
(d) subjecting LPG produced in the integrated process to olefins synthesis.

By specifically subjecting resid to resid upgrading to produce LPG and a liquid resid upgrading effluent and by subjecting said liquid resid upgrading effluent to aromatic ring opening, the propylene yield or the process of the present invention can be further improved. Furthermore, the crude oil can be upgraded to petrochemical products, particularly propylene, to a much greater extent.

As used herein, the term "resid upgrading unit" relates to a refinery unit suitable for the process of resid upgrading, which is a process for breaking the hydrocarbons comprised in the resid and/or refinery unit-derived heavy-distillate into lower boiling point hydrocarbons; see Alfke et al. (2007) loc.cit. Commercially available technologies include a delayed coker, a fluid coker, a resid FCC, a Flexicoker, a visbreaker or a catalytic hydrovisbreaker. Preferably, the resid upgrading unit may be a coking unit or a resid hydrocracker. A "coking unit" is an oil refinery processing unit that converts resid into LPG, light-distillate, middle-distillate, heavy-distillate and petroleum coke. The process thermally cracks the long chain hydrocarbon molecules in the residual oil feed into shorter chain molecules.

The feed to resid upgrading preferably comprises resid and heavy-distillate produced in the process. Such heavy-distillate may comprise the heavy-distillate produced by a steam cracker, such as carbon black oil and/or cracked distillate but may also comprise the heavy-distillate produced by resid upgrading, which may be recycled to extinction. Yet, a relatively small pitch stream may be purged from the process.

Preferably, the resid upgrading used in the process of the present invention is resid hydrocracking.

By selecting resid hydrocracking over other means for resid upgrading, the propylene yield and the carbon efficiency of the process of the present invention can be further improved.

A "resid hydrocracker" is an oil refinery processing unit that is suitable for the process of resid hydrocracking, which is a process to convert resid into LPG, light distillate, middle-distillate and heavy-distillate. Resid hydrocracking processes are well known in the art; see e.g. Alfke et al. (2007) loc.cit. Accordingly, 3 basic reactor types are employed in commercial hydrocracking which are a fixed bed (trickle bed) reactor type, an ebullated bed reactor type and slurry (entrained flow) reactor type. Fixed bed resid hydrocracking processes are well-established and are capable of processing contaminated streams such as atmospheric residues and vacuum residues to produce light- and middle-distillate which can be further processed to produce olefins and aromatics. The catalysts used in fixed bed resid hydrocracking processes commonly comprise one or more elements selected from the group consisting of Co, Mo and Ni on a refractory support, typically alumina. In case of highly contaminated feeds, the catalyst in fixed bed resid hydrocracking processes may also be replenished to a certain extend (moving bed). The process conditions commonly comprise a temperature of 350-450° C. and a pressure of 2-20 MPa gauge. Ebullated bed resid hydrocracking processes are also well-established and are inter alia characterized in that the catalyst is continuously replaced allowing the processing of highly contaminated feeds. The catalysts used in ebullated bed resid hydrocracking processes commonly comprise one or more elements selected from the group consisting of Co, Mo and Ni on a refractory support, typically alumina. The small particle size of the catalysts employed effectively increases their activity (c.f. similar formulations in forms suitable for fixed bed applications). These two factors allow ebullated bed hydrocracking processes to achieve significantly higher yields of light products and higher levels of hydrogen addition when compared to fixed bed hydrocracking units. The process conditions commonly comprise a temperature of 350-450° C. and a pressure of 5-25 MPa gauge. Slurry resid hydrocracking processes represent a combination of thermal cracking and catalytic hydrogenation to achieve high yields of distillable products from highly contaminated resid feeds. In the first liquid stage, thermal cracking and hydrocracking reactions occur simultaneously in the fluidized bed at process conditions that include a temperature of 400-500° C. and a pressure of 15-25 MPa gauge. Resid, hydrogen and catalyst are introduced at the bottom of the reactor and a fluidized bed is formed, the height of which depends on flow rate and desired conversion. In these processes catalyst is continuously replaced to achieve consistent conversion levels through an operating cycle. The catalyst may be an unsupported metal sulfide that is generated in situ within the reactor. In practice the additional costs associated with the ebullated bed and slurry phase reactors are only justified when a high conversion of highly contaminated heavy streams such as vacuum gas oils is required. Under these circumstances the limited conversion of very large molecules and the difficulties associated with catalyst deactivation make fixed bed processes relatively unattractive in the process of the present invention. Accordingly, ebullated bed and slurry reactor types are preferred due to their improved yield of light- and middle-distillate when compared to fixed bed hydrocracking. As used herein, the term "resid upgrading liquid effluent" relates to the product produced by resid upgrading excluding the gaseous products, such as methane and LPG and the heavy distillate produced by resid upgrading. The heavy-distillate produced by resid upgrading is preferably recycled to the resid upgrading unit until extinction. However, it may be necessary to purge a relatively small pitch stream. From the viewpoint of carbon efficiency, a resid hydrocracker is preferred over a coking unit as the latter produces considerable amounts of petroleum coke that cannot be upgraded to high value petrochemical products. From the viewpoint of the hydrogen balance of the integrated process, it may be preferred to select a coking unit over a resid hydrocracker as the latter consumes considerable amounts of hydrogen. Also in view of the capital expenditure and/or the operating costs it may be advantageous to select a coking unit over a resid hydrocracker.

In case the resid is further fractionated using a vacuum distillation unit to separate the resid into a vacuum gas oil fraction and vacuum residue fraction, it is preferred to subject the vacuum gasoil to vacuum gasoil hydrocracking and the vacuum resid to vacuum resid hydrocracking, wherein the heavy distillate produced by vacuum resid hydrocracking is subsequently subjected to vacuum gasoil hydrocracking. In case the present invention involves vacuum distillation, the vacuum gasoil thus obtained is preferably fed to the aromatic ring opening unit together with one or more other hydrocarbon streams that are relatively rich in aromatic hydrocarbons and which have a boiling point in the kerosene and gasoil boiling point range. Such hydrocarbon streams that are relatively rich in aromatic hydrocarbons and which have a boiling point in the kerosene and gasoil boiling point range may be selected from the group consisting of kerosene, gasoil and middle-distillate. The vacuum residue hydrocracking preferably is slurry resid hydrocracking as defined herein above.

Preferably at least 50 wt-%, more preferably at least 60 wt-%, even more preferably at least 70 wt-%, particularly preferably at least 80 wt-%, more particularly preferably at least 90 wt-% and most preferably at least 95 wt-% of the combined kerosene and gasoil produced by the crude oil distillation in the process is subjected to hydrocracking. Accordingly, preferably less than 50 wt-%, more preferably less than 40 wt-%, even more preferably less than 30 wt-%, particularly preferably less than 20 wt-%, more particularly preferably less than 10 wt-% and most preferably less 5 wt-% of the crude oil is converted into fuels in the process of the present invention.

As used herein, the term "unit for olefins synthesis" relates to a unit wherein a process for olefins synthesis is performed. This term includes any process for the conversion of hydrocarbons to olefins including, but not limited to non-catalytic processes such as pyrolysis or steam cracking, catalytic processes such as propane dehydrogenation or butane dehydrogenation, and combinations of the two such as catalytic steam cracking.

A very common process for olefins synthesis involves "pyrolysis" or "steam cracking". As used herein, the term "steam cracking" relates to a petrochemical process in which saturated hydrocarbons are broken down into smaller, often unsaturated, hydrocarbons such as ethylene and propylene. In steam cracking gaseous hydrocarbon feeds like ethane, propane and butanes, or mixtures thereof, (gas cracking) or liquid hydrocarbon feeds like naphtha or gasoil (liquid cracking) is diluted with steam and briefly heated in a furnace without the presence of oxygen. Typically, the reaction temperature is 750-900° C. and the reaction is only allowed to take place very briefly, usually with residence times of 50-1000 milliseconds. Preferably, a relatively low process pressure is to be selected of atmospheric up to 175 kPa gauge. Preferably, the hydrocarbon compounds ethane, propane and butanes are separately cracked in accordingly specialized furnaces to ensure cracking at optimal conditions. After the cracking temperature has been reached, the gas is quickly quenched to stop the reaction in a transfer line heat exchanger or inside a quenching header using quench oil. Steam cracking results in the slow deposition of coke, a form of carbon, on the reactor walls. Decoking requires the furnace to be isolated from the process and then a flow of steam or a steam/air mixture is passed through the furnace coils. This converts the hard solid carbon layer to carbon monoxide and carbon dioxide. Once this reaction is complete, the furnace is returned to service. The products produced by steam cracking depend on the composition of the feed, the hydrocarbon to steam ratio and on the cracking temperature and furnace residence time. Light hydrocarbon feeds such as ethane, propane, butane or light naphtha give product streams rich in the lighter polymer grade olefins, including ethylene, propylene, and butadiene. Heavier hydrocarbon (full range and heavy naphtha and gas oil fractions) also give products rich in aromatic hydrocarbons.

To separate the different hydrocarbon compounds produced by steam cracking the cracked gas is subjected to a fractionation unit. Such fractionation units are well known in the art and may comprise a so-called gasoline fractionator where the heavy-distillate ("carbon black oil") and the middle-distillate ("cracked distillate") are separated from the light-distillate and the gases. In the subsequent optional quench tower, most of the light-distillate produced by steam cracking ("pyrolysis gasoline" or "pygas") may be separated from the gases by condensing the light-distillate. Subsequently, the gases may be subjected to multiple compression stages wherein the remainder of the light distillate may be separated from the gases between the compression stages. Also acid gases (CO2 and H2S) may be removed between compression stages. In a following step, the gases produced by pyrolysis may be partially condensed over stages of a cascade refrigeration system to about where only the hydrogen remains in the gaseous phase. The different hydrocarbon compounds may subsequently be separated by simple distillation, wherein the ethylene, propylene and C4 olefins are the most important high-value chemicals produced by steam cracking. The methane produced by steam cracking is generally used as fuel gas, the hydrogen may be separated and recycled to processes that consume hydrogen, such as hydrocracking processes. The acetylene produced by steam cracking preferably is selectively hydrogenated to ethylene. The alkanes comprised in the cracked gas may be recycled to the process for olefin synthesis.

Preferably, the olefins synthesis as used in the present invention comprises pyrolysis of ethane and dehydrogenation of propane. By converting one or more of naphtha, kerosene and gasoil produced by crude oil distillation in the process; and refinery unit-derived light-distillate and/or refinery unit-derived middle-distillate produced in the process to LPG, the propane comprised in the LPG can be subjected to propane dehydrogenation to produce propylene and hydrogen, which has an improved propylene yield when compared to pyrolysis since in a propane dehydrogenation process substantially no undesired by-products are produced.

By selecting olefins synthesis comprising propane dehydrogenation, the overall hydrogen balance of the integrated process can be improved. A further advantage of integrating dehydrogenation process into the integrated process is that a high-purity hydrogen stream is produced, which can be used as feed to aromatic ring opening or other upstream refinery processes without expensive purification.

The term "propane dehydrogenation unit" as used herein relates to a petrochemical process unit wherein a propane feedstream is converted into a product comprising propylene and hydrogen. Accordingly, the term "butane dehydrogenation unit" relates to a process unit for converting a butane feedstream into C4 olefins. Together, processes for the dehydrogenation of lower alkanes such as propane and butanes are described as lower alkane dehydrogenation process. Processes for the dehydrogenation of lower alkanes are well-known in the art and include oxidative dehydrogenation processes and non-oxidative dehydrogenation processes. In an oxidative dehydrogenation process, the process heat is provided by partial oxidation of the lower alkane(s) in the feed. In a non-oxidative dehydrogenation process, which is preferred in the context of the present invention, the process heat for the endothermic dehydrogenation reaction is provided by external heat sources such as hot flue gases obtained by burning of fuel gas or steam. In a non-oxidative dehydrogenation process the process conditions generally comprise a temperature of 540-700° C. and an absolute pressure of 25-500 kPa. For instance, the UOP Oleflex process allows for the dehydrogenation of propane to form propylene and of (iso)butane to form (iso)butylene (or mixtures thereof) in the presence of a catalyst containing platinum supported on alumina in a moving bed reactor; see e.g. U.S. Pat. No. 4,827,072. The Uhde STAR process allows for the dehydrogenation of propane to form propylene or of butane to form butylene in the presence of a promoted platinum catalyst supported on a zinc-alumina spinel; see e.g. U.S. Pat. No. 4,926,005. The STAR process has been recently improved by applying the principle of oxydehydrogenation. In a secondary adiabatic zone in the reactor part of the hydrogen from the intermediate product is selectively converted with added oxygen to form water. This shifts the thermodynamic equilibrium to higher conversion and achieves a higher yield. Also the external heat required for the endothermic dehydrogenation reaction is partly supplied by the exothermic hydrogen conversion. The Lummus Catofin process employs a number of fixed bed reactors operating on a cyclical basis. The catalyst is activated alumina impregnated with 18-20 wt-% chromium; see e.g. EP 0 192 059 A1 and GB 2 162 082 A. The Catofin process has the advantage that it is capable of handling impurities which would poison a platinum catalyst. The products produced by a butane dehydrogenation process depend on the nature of the butane feed and the butane dehydrogenation process used. Also the Catofin process allows for the dehydrogenation of butane to form butylene; see e.g. U.S. Pat. No. 7,622,623.

Preferably, the gases fraction produced by the crude distillation unit and the refinery unit-derived gases are subjected to gas separation to separate the different components, for instance to separate methane from LPG.

As used herein, the term "gas separation unit" relates to the refinery unit that separates different compounds comprised in the gases produced by the crude distillation unit and/or refinery unit-derived gases. Compounds that may be separated to separate streams in the gas separation unit comprise ethane, propane, butanes, hydrogen and fuel gas mainly comprising methane. Any conventional method suitable for the separation of said gases may be employed in the context of the present invention. Accordingly, the gases may be subjected to multiple compression stages wherein acid gases such as CO2 and H2S may be removed between compression stages. In a following step, the gases produced may be partially condensed over stages of a cascade refrigeration system to about where only the hydrogen remains in the gaseous phase. The different hydrocarbon compounds may subsequently be separated by distillation.

Preferably, the olefins synthesis as used in the present invention comprises pyrolysis of butanes. By selecting pyrolysis of butanes over, e.g. dehydrogenation of butanes, the propylene yield of the process of the present invention can be further improved.

Preferably, the process of the present invention further comprises subjecting part of the liquid resid upgrading effluent, and optionally light-distillate produced by aromatic ring opening, to fluid catalytic cracking to produce light-distillate, middle-distillate and olefins, and subjecting said middle-distillate produced by fluid catalytic cracking to aromatic ring opening.

By subjecting the liquid resid upgrading effluent to fluid catalytic cracking, the hydrogen consumption of the process of the present invention can be reduced when compared to a process wherein the heavy-distillate produced by resid upgrading is recycled to said resid upgrading to extinction. Furthermore, by selecting a process comprising fluid catalytic cracking, the light-distillate produced by aromatic ring opening can be more efficiently upgraded to petrochemical products.

As used herein, the term "fluid catalytic cracker unit" or "FCC unit" relates to a refinery unit to convert high-boiling, high-molecular weight hydrocarbon fractions of petroleum crude oils to lower boiling point hydrocarbon fractions and olefinic gases. In a FCC unit, cracking takes place generally using a very active zeolite-based catalyst in a short-contact time vertical or upward-sloped pipe called the "riser". Preheated feed is sprayed into the base of the riser via feed nozzles where it contacts extremely hot fluidized catalyst.

Preferred process conditions used for fluid catalytic cracking generally include a temperature of 425-700° C. and a pressure of 10-800 kPa gauge. The hot catalyst vaporizes the feed and catalyzes the cracking reactions that break down the high-molecular weight hydrocarbons into lighter components including LPG, light-distillate and middle-distillate. The catalyst/hydrocarbon mixture flows upward through the riser for a few seconds, and then the mixture is separated via cyclones. The catalyst-free hydrocarbons are routed to a main fractionator (a component of the FCC unit for separation into fuel gas, LPG, light distillate, middle distillate and heavy-distillate). "Spent" catalyst is disengaged from the cracked hydrocarbon vapors and sent to a stripper where it is contacted with steam to remove hydrocarbons remaining in the catalyst pores. The "spent" catalyst then flows into a fluidized-bed regenerator where air (or in some cases air plus oxygen) is used to burn off the coke to restore catalyst activity and also provide the necessary heat for the next reaction cycle, cracking being an endothermic reaction. The "regenerated" catalyst then flows to the base of the riser, repeating the cycle. The process of the present invention may comprise several FCC units operated at different process conditions, depending on the hydrocarbon feed and the desired product slate. As used herein, the term "low-severity FCC" or "refinery FCC" relates to a FCC process that is optimized towards the production of light-distillate that is relatively rich in aromatics ("FCC-gasoline"). As most conventional refineries are optimized towards gasoline production, conventional FCC process operating conditions can be considered to represent low-severity FCC. Preferred process conditions used for refinery FCC generally include a temperature of 425-570° C. and a pressure of 10-800 kPa gauge. As used herein, the term "high-severity FCC" or "petrochemicals FCC" relates to a FCC process that is optimized towards the production of olefins. High-severity FCC processes are known from the prior art and are inter alia described in EP 0 909 804 A2, EP 0 909 582 A1 and U.S. Pat. No. 5,846,402. Preferred process conditions used for high-severity FCC generally include a temperature of 540-700° C. and a pressure of 10-800 kPa gauge. In the present invention a high-severity FCC is preferred.

The process of the present invention may require removal of sulfur from certain crude oil fractions to prevent catalyst deactivation in downstream refinery processes, such as catalytic reforming or fluid catalytic cracking. Such a hydrodesulfurization process is performed in a "HDS unit" or "hydrotreater"; see Alfke (2007) loc. cit. Generally, the hydrodesulfurization reaction takes place in a fixed-bed reactor at elevated temperatures of 200-425° C., preferably of 300-400° C. and elevated pressures of 1-20 MPa gauge, preferably 1-13 MPa gauge in the presence of a catalyst comprising elements selected from the group consisting of Ni, Mo, Co, W and Pt, with or without promoters, supported on alumina, wherein the catalyst is in a sulfide form.

Furthermore, the propylene yield can be further improved by converting butenes and ethylene produced in the process of the present invention to propylene using the methathesis process. The metathesis process is well known in the art and is inter alia described in U.S. Pat. No. 4,575,575.

Figure 2:
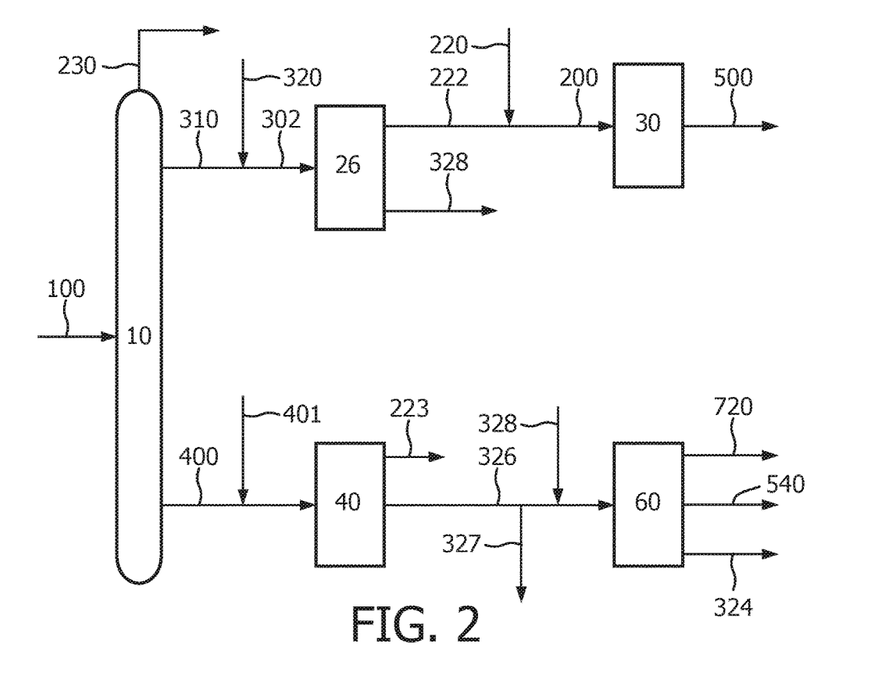
FIG. 2 depicts an embodiment in accordance with the present invention.
Figure 3:
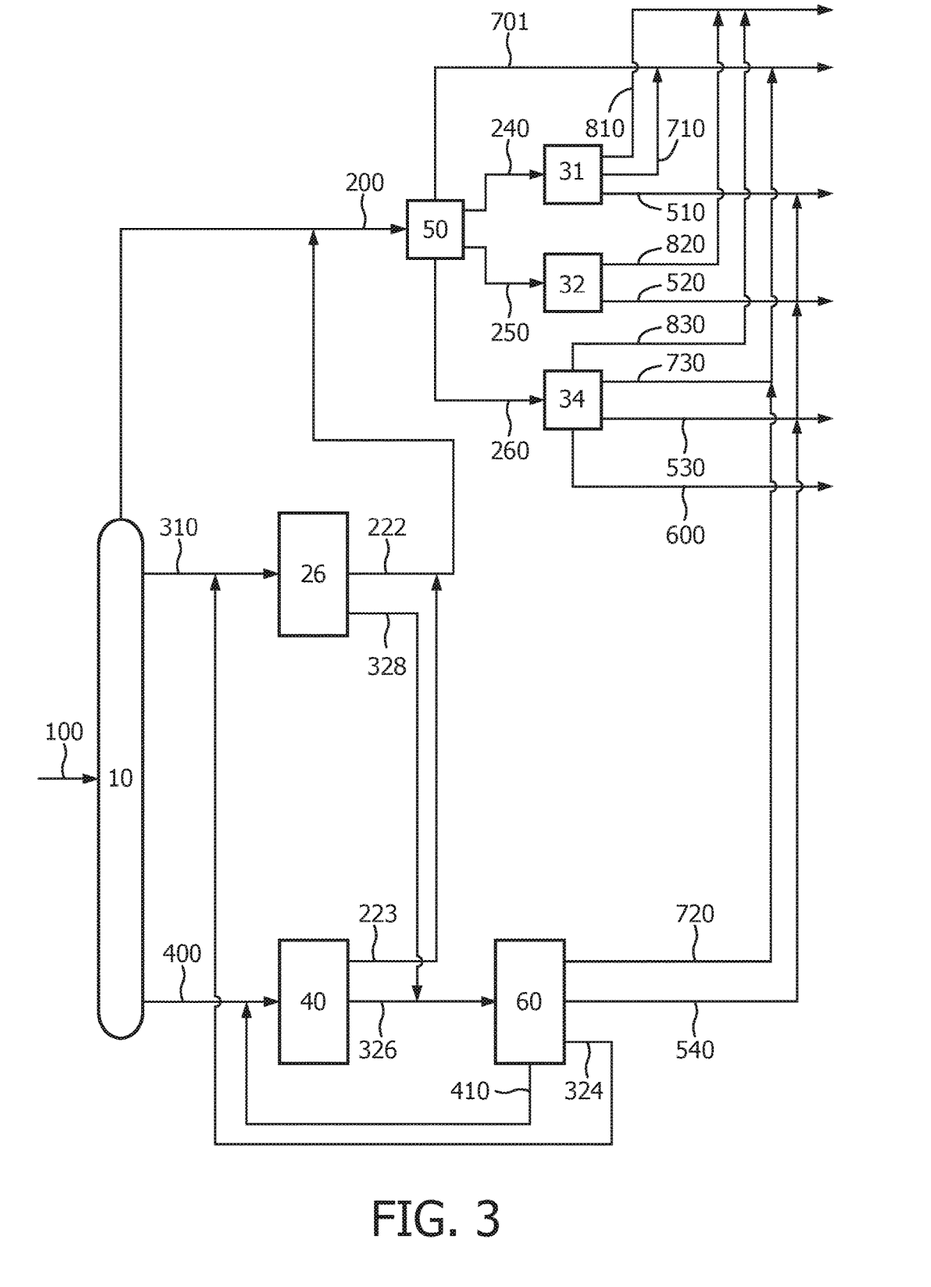
FIG. 3 depicts an embodiment in accordance with the present invention.

In a further aspect, the invention also relates to a process installation suitable for performing the process of the invention. This process installation and the process as performed in said process installation is presented in FIGS. 1-3 (FIG. 1-3).

Accordingly, the present invention further provides a process installation to convert crude oil into petrochemical products comprising a crude distillation unit (10) comprising an inlet for crude oil (100) and at least one outlet for kerosene and/or gasoil (310);
an aromatic ring opening unit (26) comprising an inlet for a hydrocarbon feed to aromatic ring opening (302) and an outlet for LPG (222); and
a unit for the olefins synthesis (30) comprising an inlet for LPG produced by the integrated petrochemical process installation (200) and an outlet for olefins (500),
wherein said hydrocarbon feed to aromatic ring opening comprises:
  kerosene and/or gasoil produced by the crude oil distillation unit (10); and
  refinery unit-derived middle-distillate produced the integrated petrochemical process installation.

Figure 1:
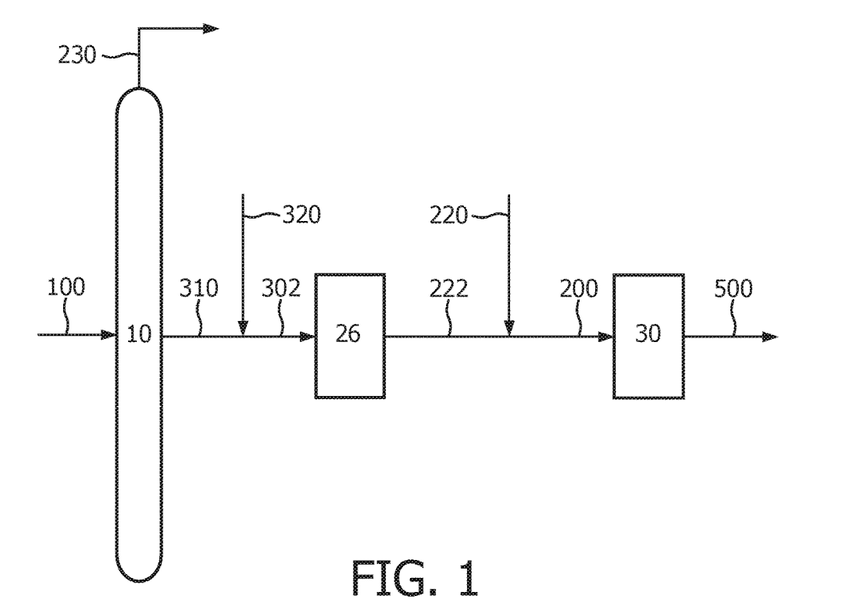
FIG. 1 depicts an embodiment in accordance with the present invention.

This aspect of the present invention is presented in FIG. 1 (FIG. 1).

The crude distillation unit (10) preferably further comprises an outlet for the gases fraction (230). The LPG produced by aromatic ring opening (222) and LPG comprised in the gases fraction and refinery unit-derived LPG produced in the integrated process (220) may be combined to form the inlet for LPG produced by the integrated petrochemical process installation (200). The crude distillation unit (10) preferably further comprises an outlet for the naphtha fraction. The naphtha produced by the crude distillation unit may be combined with the kerosene and/or the gasoil produced by the crude oil distillation unit and subsequently subjected to aromatic ring opening. Furthermore, kerosene and/or gasoil, and optionally the naphtha, produced by the crude oil distillation unit (310) may be combined with refinery unit-derived middle-distillate and optionally the refinery unit-derived light-distillate produced the integrated petrochemical process installation (320) to form the inlet for a hydrocarbon feed to aromatic ring opening (302).

As used herein, the term "an inlet for X" or "an outlet of X", wherein "X" is a given hydrocarbon fraction or the like relates to an inlet or outlet for a stream comprising said hydrocarbon fraction or the like. In case of an outlet for X is directly connected to a downstream refinery unit comprising an inlet for X, said direct connection may comprise further units such as heat exchangers, separation and/or purification units to remove undesired compounds comprised in said stream and the like.

If, in the context of the present invention, a refinery unit is fed with more than one feed stream, said feed streams may be combined to form one single inlet into the refinery unit or may form separate inlets to the refinery unit.

Furthermore, the crude distillation unit (10) may comprise an outlet for resid (400). The process installation of the present invention may further comprise a resid upgrading unit (40) comprising an inlet for resid (400) and refinery unit-derived heavy-distillate (401), an outlet for LPG produced by resid upgrading (223) and an outlet for liquid resid upgrading effluent (326). This aspect of the present invention is presented in FIG. 2 (FIG. 2). The liquid resid upgrading effluent (326) comprises light-distillate and middle-distillate that preferably is subjected to aromatic ring opening.

The process installation of the present invention may further comprise a fluid catalytic cracking unit (60) comprising an inlet for a part of the liquid resid upgrading effluent (326) and optionally light-distillate produced by aromatic ring opening (328) and an outlet for middle-distillate, and optionally light-distillate, produced by fluid catalytic cracking (324) and olefins produced by fluid catalytic cracking (540). This aspect of the present invention is presented in FIG. 2 (FIG. 2).

The fluid catalytic cracking unit (60) may further comprise an outlet for methane (720). Furthermore, the process installation comprising a fluid catalytic cracking unit (60) may comprise an outlet for the part of the liquid resid upgrading effluent that is not subjected to fluid catalytic cracking (327), which may be recycled to the resid upgrading unit (40). In case part of the light-distillate produced by aromatic ring opening is subjected to fluid catalytic cracking, the process installation unit comprises a aromatic ring opening unit (26) having an outlet for light-distillate (328) which is combined with for a part of the liquid resid upgrading effluent (326). The fluid catalytic cracking unit (60) may further comprise an outlet for heavy-distillate produced fluid catalytic cracking (410) which may be recycled to the resid upgrading unit (40) to further upgrade said heavy-distillate; see also FIG. 3.

Preferably, the process installation of the present invention further comprises:

a gas separation unit (50) comprising an inlet for gases produced in the integrated process (200), an outlet for ethane (240) and an outlet for propane (250);

an ethane cracker (31) comprising an inlet for ethane (240) and an outlet for ethylene (510); and a propane dehydrogenation unit (32) comprising an inlet for propane (250) and an outlet for propylene (520). This aspect of the present invention is presented in FIG. 3 (FIG. 3).

The gas separation unit (50) may further comprise an outlet for methane (701). The ethane cracker (31) may further comprise an outlet for hydrogen produced by ethane cracking (810) and an outlet for methane produced by ethane cracking (710). The propane dehydrogenation unit (32) may further comprise an outlet for hydrogen produced by propane dehydrogenation (820).

The gas separation unit (50) may further comprise an outlet for butanes (260), wherein said process installation further comprises a butane cracker (34) comprising an inlet for butanes (260) and an outlet for olefins (530) and an outlet for BTX (600). The BTX is preferably comprised in the pygas produced by said butane cracker (34). This aspect of the present invention is presented in FIG. 3 (FIG. 3). The butane cracker (34) may further comprise an outlet for hydrogen produced by butane cracking (830) and an outlet for methane produced by butane cracking (730).

In this respect, it is to be noted that the cracked gas produced by the different cracker units may be combined and subjected to a single separation section to separate the olefins and BTX comprised in the cracked gas from the other components.

The present invention further provides the use of the process installation according to the present invention for converting crude oil into petrochemical products comprising olefins and BTX.

A further preferred feature of the present invention is that all non-desired products, such as non-high-value petrochemicals may be recycled to the appropriate unit to convert such a non-desired product to either a desired product (e.g. a high-value petrochemical) or to a product that is a suitable as feed to a different unit. This aspect of the present invention is presented in FIG. 3 (FIG. 3).

In the process and the process installation of the present invention, all methane produced is collected and preferably subjected to a separation process to provide fuel gas. Said fuel gas is preferably used to provide the process heat in the form of hot flue gases produced by burning the fuel gas or by forming steam. Alternatively, the methane can be subjected to steam reforming to produce hydrogen. Also the undesired side products produced by e.g. steam cracking may be recycled. For instance, the carbon black oil and cracked distillate produced by steam cracking may be recycled to aromatic ring opening.

The different units operated in the process or the process installation of the present invention are furthermore integrated by feeding the hydrogen produced in certain processes, such as in olefins synthesis, as a feedstream to processes that need hydrogen as a feed, such as in hydrocracking. In case the process and the process installation is a net consumer of hydrogen (i.e. during start-up of the process or the process installation or because all hydrogen consuming processes consume more hydrogen than produced by all hydrogen producing processes), reforming of additional methane or fuel gas than the fuel gas produced by the process or the process installation of the present invention may be required.

The following numerical references are used in FIGS. 1-3:
10 crude distillation unit
26 aromatic ring opening unit
30 unit for olefins synthesis
31 ethane cracker
32 propane dehydrogenation unit
34 butanes cracker
40 resid upgrading unit, preferably a resid hydrocracker
50 gas separation unit
60 fluid catalytic cracking unit
100 crude oil
200 LPG produced in the integrated process
220 gases fraction and refinery unit-derived LPG produced in the integrated process
222 LPG produced by aromatic ring opening
223 LPG produced by resid upgrading
230 gases fraction
240 ethane
250 propane
260 butanes
302 hydrocarbon feed to aromatic ring opening
310 kerosene and/or gasoil, and optionally the naphtha, produced by crude oil distillation unit
320 refinery unit-derived middle-distillate and optionally the refinery unit-derived light-distillate produced the integrated petrochemical process installation
324 middle-distillate, and optionally light-distillate, produced by fluid catalytic cracking
326 resid upgrading liquid effluent
327 part of the liquid resid upgrading effluent that is not subjected to fluid catalytic cracking
328 light-distillate produced by aromatic ring opening
400 resid
401 refinery unit-derived heavy-distillate
410 heavy-distillate produced by fluid catalytic cracking
500 olefins
510 ethylene produced by ethane cracking
520 propylene produced by propane dehydrogenation unit
530 C4 olefins produced by butanes cracking
540 olefins produced by fluid catalytic cracking
600 BTX
701 methane produced by gas separation
710 methane produced by ethane cracking
720 methane produced by fluid catalytic cracking
730 methane produced by butanes cracking
810 hydrogen produced by ethane cracking
820 hydrogen produced by propane dehydrogenation
830 hydrogen produced by butanes cracking Although the invention has been described in detail for purposes of illustration, it is understood that such detail is solely for that purpose and variations can be made therein by those skilled in the art without departing from the spirit and scope of the invention as defined in the claims.

It is further noted that the invention relates to all possible combinations of features described herein, preferred in particular are those combinations of features that are present in the claims.

It is noted that the term "comprising" does not exclude the presence of other elements. However, it is also to be understood that a description on a product comprising certain components also discloses a product consisting of these components. Similarly, it is also to be understood that a description on a process comprising certain steps also discloses a process consisting of these steps.

The present invention will now be more fully described by the following non-limiting Examples.

Comparative Example 1

The experimental data as provided herein were obtained by flowsheet modelling in Aspen Plus. The steam cracking kinetics were taken into account rigorously (software for steam cracker product slate calculations). The following steam cracker furnace conditions were applied: ethane and propane furnaces: COT (Coil Outlet temperature)=845° C. and steam-to-oil-ratio=0.37, C4-furnaces and liquid furnaces: Coil Outlet temperature=820° C. and Steam-to-oil-ratio=0.37.

For the aromatic ring opening a reaction scheme has been used in which all aromatic, naphthenic and paraffinic compounds were converted into LPG. The product slates from propane dehydrogenation were based on literature data. The resid hydrocracker and the FCC unit were modelled based on data reported in open literature.

In Comparative Example 1, Arabian light crude oil is distilled in an atmospheric distillation unit. All fractions except the resid are being steam cracked. The fractions sent to the steam cracker comprise LPG, naphtha, kerosene and gasoil fractions. The cut point for the resid is 350° C. The total fraction of the crude being sent to the steam cracker amounts to 52 wt % of the crude. In the steam cracker the above mentioned crude fractions are being cracked in the furnaces. The results are provided in table 1 as provided herein below.

The products that are derived from the crude oil are divided into petrochemicals (olefins and BTXE, which is an acronym for BTX+ethylbenzene) and other products (hydrogen, methane and heavy fractions comprising C9 resin feed, cracked distillate, carbon black oil and resid). The total amount sums up to 100% of the total crude, since the resid is also taken into account. From the product slate of the crude oil the carbon efficiency is determined as: (Total Carbon Weight in petrochemicals)/(Total Carbon Weight in Crude).

For the Comparative Example the propylene yield is 8 wt-% of the total crude.

Example 1

Example 1 is identical to the Comparative Example except for the following:

The naphtha, kerosene and gas oil fractions (cut point 350° C.) of the crude distillation are subjected to aromatic ring opening that is operated under process conditions to open all aromatic rings and convert the remaining paraffins and naphthenes into LPG (intermediate). This LPG is separated into an ethane-, propane- and butane fraction. The ethane and butane fractions are being steam cracked. The propane fraction is dehydrogenated into propylene (with ultimate selectivities of propane to propylene 90%).

Table 1 as provided herein below displays the total product slate from the steam cracker (cracked lights and ethane and butane) and from the propane dehydrogenation unit, in wt-% of the total crude. The table also contains the remaining atmospheric residue fraction.

For Example 1 the propylene yield is 29 wt-% of the total crude.

Example 2

Example 2 is identical to Example 1 except for the following:

First, the resid is upgraded in a resid hydrocracker to produce gases, light-distillate and middle-distillate. The gases produced by resid hydrocracking are steam cracked. The light-distillate and middle-distillate produced by resid hydrocracking are subjected to aromatic ring opening that is operated under process conditions to open all aromatic rings and convert the remaining paraffins and naphthenes into LPG (intermediate). This LPG is separated into an ethane-, propane- and butane fraction. The ethane and butane fractions are steam cracked. The propane fraction is dehydrogenated into propylene (with ultimate selectivities of propane to propylene 90%).

Furthermore, the heavy part of the cracker effluent (C9 resin feed, cracked distillate and carbon black oil) is being recycled to the resid hydrocracker. The ultimate conversion in the resid hydrocracker is close to completion (the pitch of the resid hydrocracker is 2 wt % of the crude).

Table 1 as provided herein below displays the total product slate of the crude oil from the steam cracker (cracked products of lights, naphtha and LPG) and from the propane dehydrogenation unit in wt % of the total crude. The product slate also contains the pitch of the hydrocracker (2 wt % of the crude).

For Example 2 the propylene yield is 55 wt-% of the total crude.

Example 3

Example 3 is identical to Example 2 except for the following:

The resid hydrocracker does not crack to extinction but the conversion to gases, light-distillate and middle-distillate fractions is 37.5%. The remaining product from the resid hydrocracker (heavy distillate and bottom) is sent to a FCC unit, to produce lights and FCC naphtha. The lights are sent to the steam cracker where the olefins in the lights are separated from the LPG. This LPG is separated into an ethane-, propane- and butane fraction. The ethane and butane fractions are steam cracked. The propane fraction is dehydrogenated into propylene (with ultimate selectivities of propane to propylene 90%). The FCC naphtha is subjected to aromatic ring opening under process conditions to open all aromatic rings and convert the remaining paraffins and naphthenes into LPG (intermediate). This LPG is separated into an ethane-, propane- and butane fraction. The ethane and butane fractions are steam cracked. The propane fraction is dehydrogenated into propylene (with ultimate selectivities of propane to propylene 90%). The LCO (light cyclic oil) from the FCC unit is recycled to the resid hydrocracker.

Table 1 as provided herein below displays the total product slate of the crude oil from the steam cracker (cracked products of lights, naphtha and LPG) and from the propane dehydrogenation unit in wt % of the total crude. The product slate also contains the pitch of the hydrocracker and the coke of the FCC unit (together 4 wt % of the crude).

For example 3 the propylene yield is 51 wt-% of the total crude.

TABLE 1

| | Comparative Example | Example 1 | Example 2 | Example 3 |
|---|---|---|---|---|
| Petrochemicals (wt-% of crude) | | | | |
| Ethylene | 15% | 15% | 29% | 27% |
| Propylene | 8% | 29% | 55% | 51% |
| Butadiene | 2% | 0% | 1% | 1% |
| 1-butene | 1% | 1% | 2% | 4% |
| Isobutene | 1% | 0% | 1% | 2% |
| Isoprene | 0% | 0% | 0% | 0% |
| Cyclopentadiene | 1% | 0% | 0% | 0% |
| Benzene | 4% | 0% | 1% | 1% |
| Toluene | 2% | 0% | 0% | 0% |
| Xylene | 1% | 0% | 0% | 0% |
| Ethylbenzene | 1% | 0% | 0% | 0% |
| Other components (wt-% of crude) | | | | |
| hydrogen | 1% | 2% | 4% | 4% |
| methane | 7% | 3% | 6% | 6% |
| Heavy components | 56% | 48% | 0% | 0% |
| RHC pitch and FCC coke | 0% | 0% | 2% | 4% |
| Carbon efficiency | 38.0% | 47.6% | 92.5 | 88.6 |

It is claimed:

1. A method of processing crude oil, the method comprising:
   (a) subjecting the crude oil to crude oil distillation to produce a gases fraction, resid and at least one of kerosene or gasoil;
   (b) separating the resid into vacuum gasoil and vacuum residue;
   (c) subjecting the vacuum gasoil to vacuum gasoil hydrocracking to produce at least some liquefied petroleum gas (LPG);
   (d) subjecting the vacuum residue to vacuum residue hydrocracking to produce heavy-distillate, liquefied petroleum gas (LPG) and middle-distillate;
   (e) subjecting the heavy-distillate and/or middle-distillate produced in step (d) to hydrocracking to produce liquefied petroleum gas (LPG); and
   (f) subjecting the LPG produced in one or more of steps (c)-(e) to olefin synthesis.

2. The method of claim 1, wherein olefin synthesis comprises steam cracking and/or catalytic dehydrogenation.

3. The method of claim 2, wherein the steam cracking comprises:
   separating C2-C4 paraffins from a gaseous stream produced by the steam cracking, further separating C2-C4 paraffins into individual streams, each stream predominantly comprising C2 paraffins, C3 paraffins and C4 paraffins, respectively; and
   feeding each individual stream to a specific furnace section of said steam cracker unit.

4. The method of claim 1, wherein the reaction conditions of step (e) comprises a temperature of 200-600° C., a pressure of 1-12 MPa, and a hydrogen fraction of 5-30 wt. % based on weight of hydrocarbons in the reaction.

5. The method of claim 1, further comprising:
   separating a gaseous fraction into a stream comprising LPG and an off-gas stream comprising methane and/or hydrogen;
   flowing the off-gas stream in a steam cracking unit to provide fuel for heating a furnace of the steam cracking unit.

6. The method of claim 1, wherein steps (c) and (e) are carried out in the same hydrocracking unit.

7. A method of processing crude oil, the method comprising:
   (a) subjecting said crude oil to crude oil distillation to produce a gases fraction, resid and at least one of kerosene or gasoil;
   (b) separating the resid into vacuum gasoil and vacuum residue;
   (c) subjecting the vacuum gasoil to vacuum gasoil hydrocracking to produce liquefied petroleum gas (LPG);
   (d) subjecting the vacuum residue to vacuum residue hydrocracking to produce additional vacuum gasoil, liquefied petroleum gas (LPG) and middle-distillate; and
   (e) subjecting the additional vacuum gasoil to vacuum gasoil hydrocracking.

8. The method of claim 7, further comprising contacting the middle-distillate with hydrogen in the presence of a catalyst under reaction conditions sufficient to produce LPG.

9. The method of claim 8, wherein the reaction conditions comprise a temperature of 200-600° C., a pressure of 1-12 MPa, and a hydrogen fraction of 5-30 wt. % based on weight of hydrocarbons.

10. The method of claim 8, wherein the catalyst in the contacting step comprises a mixture of Ni, W and Mo and one or more of Pd, Rh, Ru, Ir, Os, Cu, Co, Ni, Pt, Fe, Zn, Ga, In, Mo, W, and V in metallic or metal sulphide form.

11. The method of claim 8, further comprising subjecting the LPG produced by vacuum gasoil hydrocracking, vacuum resid hydrocracking, and/or the contacting step to olefins synthesis.

12. The method of claim 11, wherein the olefin synthesis comprises steam cracking and/or catalytic dehydrogenation.

13. The method of claim 7, further comprising subjecting the LPG produced by vacuum gasoil hydrocracking to olefins synthesis.

14. The method of claim 13, wherein the reaction conditions comprise a temperature of 200-600° C., a pressure of 1-12 MPa, and a hydrogen fraction of 5-30 wt. % based on weight of hydrocarbons.

15. The method of claim 8, further comprising subjecting the LPG produced by vacuum resid hydrocracking, and/or the contacting step to olefins synthesis.

16. The method of claim 8, further comprising subjecting the LPG produced by the contacting step to olefins synthesis.

17. The method of claim 16, wherein the olefin synthesis comprises steam cracking and/or catalytic dehydrogenation.

* * * * *